United States Patent [19]

Ishida

[11] 4,173,071
[45] Nov. 6, 1979

[54] KNIFE HAVING AN EXCHANGEABLE BLADE

[75] Inventor: Minoru Ishida, Gifu, Japan

[73] Assignee: Feather Safety Razor Co., Ltd., Osaka, Japan

[21] Appl. No.: 874,174

[22] Filed: Feb. 1, 1978

[30] Foreign Application Priority Data

Feb. 2, 1977 [JP] Japan ............................ 52/10574[U]

[51] Int. Cl.² .............................................. B26B 1/00
[52] U.S. Cl. .................................... 30/339; 145/61 D
[58] Field of Search ................ 30/339, 337; 145/61 D

[56] References Cited

U.S. PATENT DOCUMENTS

| 1,596,277 | 8/1926 | Langbein | 30/337 |
| 2,454,353 | 11/1948 | Steele | 30/339 |
| 2,655,723 | 10/1953 | Steele | 30/339 |
| 2,708,313 | 5/1955 | Steele | 30/339 |
| 3,373,491 | 3/1968 | Montelius | 30/339 |

FOREIGN PATENT DOCUMENTS

| 2299946 | 9/1976 | France | 30/339 |
| 183404 | 7/1922 | United Kingdom | 30/339 |

*Primary Examiner*—Robert L. Spruill
*Assistant Examiner*—J. T. Zatarga

*Attorney, Agent, or Firm*—Pollock, Vande Sande & Priddy

[57] ABSTRACT

A knife is composed of a gripping handle and a blade adapted to be detachably mounted on the handle. The blade is formed with a profiled slot at a base portion to be secured to the handle. The handle has a blade mounting portion which comprises a supporting surface formed at one end portion of the handle for receiving the blade thereon, a stud projecting from the supporting surface and adapted to be inserted through the slot, a first stopper formed on the supporting surface at such a position that a portion of the back of the blade placed on the supporting surface with the slot having the stud extending therethrough can bear against the first stopper, a second stopper formed on the supporting surface at a position spaced from the first stopper so that another portion of the back of the blade placed on the supporting surface can bear against the second stopper, and a latch plate fixedly mounted on the free end of the stud and having a profiled contour such that the latch plate can pass through the slot at a predetermined angular position of the blade relative to the handle and prevent the blade from slipping off from the stud at the position in which the blade is held fixedly by the first and second stoppers in cooperation with the stud.

9 Claims, 4 Drawing Figures

KNIFE HAVING AN EXCHANGEABLE BLADE

The present invention relates to a knife and in particular to a knife or scalpel having an exchangeable blade.

BACKGROUND OF THE INVENTION

A knife or scalpel which is composed of a gripping handle and a blade adapted to be detachably mounted on the gripping handle at an end has been hitherto known. To this end, the blade has a profiled slot formed therein, while the handle has a blade mounting extension or projection of such a profile that a projection can be easily received in the profiled slot and brought to the closely engaging position by appropriately displacing the blade relative to the mounting projection. The hitherto known knife however suffers from the drawback that it is difficult to support the blade firmly by means of the mounting projection without any looseness, because of, for example, the inevitable tolerance that exists in the geometrical configurations of the mounting extension and the slot which are engaged with each other. Such drawback can become serious, particularly in the case of a surgeon's knife, or scalpel.

SUMMARY OF THE INVENTION

An object of the invention is to provide a knife of a detachable or exchangeable blade type having a blade mounting structure which assures a firm support of the blade without incurring any looseness.

Another object of the invention is to provide a blade detachable type knife having a blade mounting means which allows the blade to be firmly fixed to the handle of the knife through simple manipulation.

With above objects in view, there is provided according to one aspect of the invention a knife including a gripping handle and a blade which is adapted to be detachably mounted on the gripping handle, wherein the blade is formed with a through-hole at a base portion to be secured to the handle, while the handle includes a gripping portion and blade mounting means at one end portion thereof, the blade mounting means comprising a supporting surface formed as an offset form the plane of a side surface of the handle for receiving the blade thereon, a stud projecting from the supporting surface and adapted to be inserted through the through-hole, a first stopper member provided on the supporting surface at such a position that a first portion of the back of the blade placed on the supporting surface with the stud extending through the through-hole can bear against the first stopper, a second stopper member provided on the supporting surface at a position spaced from the first stopper member such that a second portion of the back of the blade placed on the supporting surface can bear against the second stopper, and latch means mounted fixedly on the stud at the free end thereof for preventing the blade from being inadvertently detached from the handle, whereby the blade is held fixedly by the first and second stoppers in cooperation with the stud.

DETAILED DESCRIPTION OF THE PREFERRED EMBODIMENT

Figure 1:
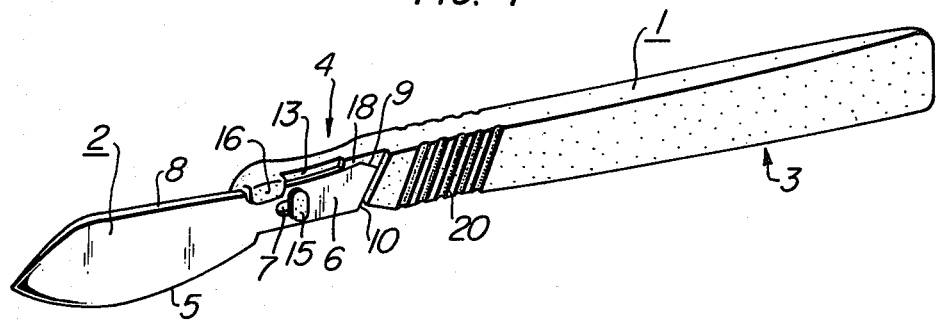
FIG. 1 shows in a perspective view a knife according to the invention in the state in which a blade is mounted on a handle.
Figure 2:
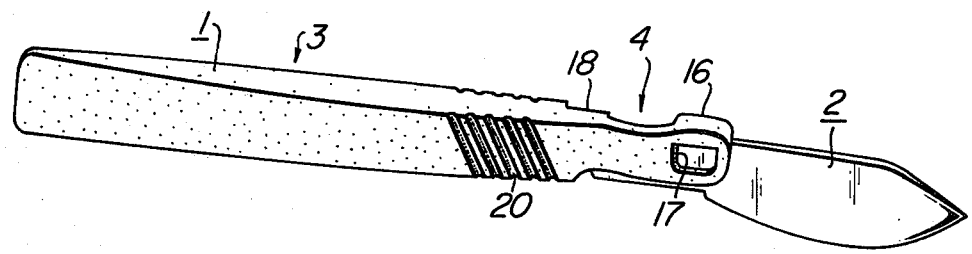
FIG. 2 shows rear side of the knife shown in FIG. 1.

Referring to the drawings and in particular to FIG. 1, a knife or scalpel device according to the invention comprises a handle generally denoted by reference numeral 1 and a blade 2 which is adapted to be removably mounted on the handle 1. To this end, the handle 1 is composed of a grip 3 and a blade mounting portion generally designated by reference numeral 4.

Figure 3:
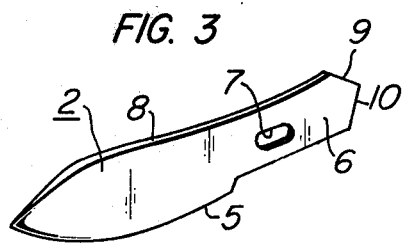
FIG. 3 is a perspective view showing a blade.

Referring to FIG. 3, the blade 2 includes an edge 5 and a base portion 6 at which the blade 2 is mounted on the handle 1. A longitudinally elongated slot 7 is formed in the base portion 6 for the purpose which will be described hereinafter. Reference numeral 8 denotes the back of the blade 2 which is formed with a beveled shoulder portion 9 at the rear end thereof.

Figure 4:
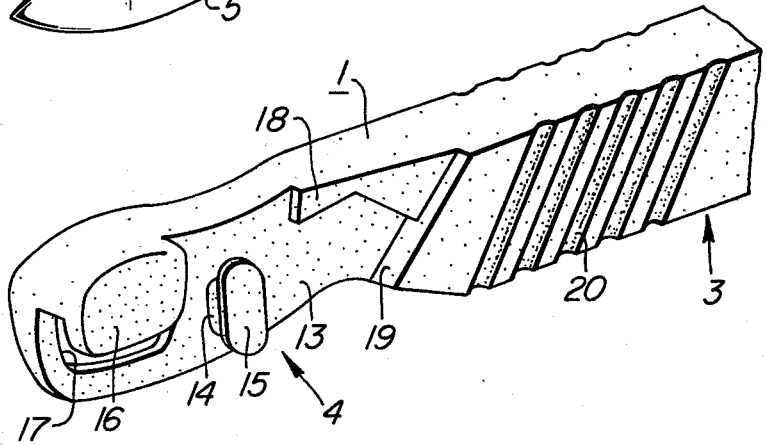
FIG. 4 is a fragmental enlarged perspective view showing a blade mounting portion of the handle.

Referring to FIG. 4 which shows the blade mounting portion 4 of the handle 1 in an enlarged scale, the mounting portion 4 is formed integrally with the grip 3 of a material having some resiliency and has a flat supporting surface 13 which is offset inwardly from the plane of a side surface of the grip 3 so as to receive thereon the blade 2. In other words, the thickness of the blade mounting portion 4 is selected to be smaller than that of the grip 3 at least by the thickness of the blade 2. At a middle portion of the supporting surface 13, there is formed integrally a projecting stud 14 which has a diameter substantially corresponding to the width of the slot 7 formed in the blade 2 so that the stud 14 may be snugly received within the slot 7. Further, the length of the projecting stud 14 is selected so as to substantially correspond to the thickness of the base portion 6 of the blade 2. A latch member 15 is provided fixedly on the top of the projecting stud 14 and has a geometrical configuration which is complementary to that of the slot 7 formed in the blade 2 so that the latch 15 may pass through the slot 7 upon mounting of the blade 2 on the mounting portion 4 of the handle 1. In this connection, it is to be noted that the latch member 15 extends substantially transversely of the longitudinal axis of the handle 1 for the reason described hereinafter.

The offset or recessed supporting surface 13 is defined by a wall 19 at the end which is contiguous to the grip 3. In the case of the illustrated embodiment, this wall 19 is slanted relative to the axis of the handle 1 so that the rear end 10 of the blade 2 will snugly bear on the wall 19 when the blade 2 is mounted. Further, distance between the wall 19 and the right-hand side periphery of the stud 14 (as viewed in FIG. 4) is selected to be substantially equal to or slightly smaller than the distance between the rear end 10 and the right-hand side edge of the slot 7 of the blade 2, as viewed in FIG. 3. Provided on the supporting surface 13 at the upper region thereof preferably in flush with the top of the blade mounting portion 4 are a first stopper member 16 and a second stopper member 18 which are disposed so axially distanced from each other at such positions that the back 8 of the blade 2 will abut on the first stopper 16, while the beveled shoulder 9 will bear against the second stopper 18 upon mounting the blade 2, as can be seen from FIG. 1. In more particular, the first stopper 16 is of an inverted L-like cross-section and has a suspending leg portion which defines in cooperation with the flat supporting surface 13 a gap of a size substantially corresponding to the thickness of the blade 2, so that the latter can be snugly accommodated within the gap. The second stopper member 18 which is disposed at the rear end side of the supporting surface 13 has a lower edge of a shape complementary to that of the beveled shoulder portion 9 of the blade 2, thereby to assure that the beveled shoulder portion 9 of the blade 2 will closely and firmly bear against the stopper 18 (refer to FIG. 1) when the blade 2 is mounted. In this connection, it is noted that the thickness of the second stopper 18 is selected smaller than the depth of the offset supporting surface 13, as can be clearly seen from FIG. 4, with a view to facilitating the mounting of the blade 2. The positional relationship of the first and second stoppers 16 and 18 relative to the stud 14 is so selected that the blade 2 can be securely held by these three members without any looseness.

A through-hole or aperture 17 which is formed in the mounting portion 4 in opposition to the suspending leg of the first stopper member 16 serves to allow water or the like cleaning medium to pass therethrough when the knife is washed or rinsed.

Indents 20 formed in the handle 1 serve to assure that the knife can be easily and firmly held by a hand of operator.

When the blade 2 is to be mounted on the mounting portion 4 of the handle, the former is first positioned so as to extend orthogonally to the axis of the handle 1 with the slot 7 aligned with the latch 15. Subsequently, the blade 2 is pressed toward the mounting surface 13 with the latch 15 passing through the slot 7 and rotated in the clockwise direction as viewed in FIG. 4 about the stud 14 until the back 8 and the shoulder portion 9 of the blade 2 have attained the position to bear against the delimiting lower edges of the first and second stopper members 16 and 18, respectively. Due to the small thickness of the second stopper member 18 and some resiliency of the mounting portion 4, the base portion 6 of the blade 2 can easily move across the second stopper 18 to the position at which the shoulder portion 9 bears against the delimiting lower edge of the stopper 18. Thus, the blade 2 is firmly mounted on the handle 1 in alignment with the latter, with one face of the blade 2 closely contacting the supporting surface 13 as can be seen from FIG. 1. Since the length of the latch 15 is greater than the width of the slot 7, the blade 2 will never slip off in the mounted state.

When the blade 2 is to be removed from the handle 1, the procedure described above is merely reversed. Namely, the shoulder portion 9 of the blade 2 is disengaged from the second stopper member 18 by slightly bending the mounting portion 4 of the handle 1 by making use of the resiliency thereof and then the blade 2 is rotated about the stud 14 in the counter-clockwise direction to the position at which the latch 15 can pass through the slot 7.

As hereinbefore described, the handle 1 having the grip 3 and the blade mounting portion 4 may be made of a plastic or other material having some resiliency in a form of an integrated unit. In the above discussion, the movement of the blade 2 across the stopper 18 of small thickness upon mounting and dismounting the blade is assured by the resiliency of the blade mounting portion 4. However, this blade movement may be assured by primarily the resiliency of the base portion 6 of the blade, or the resiliency of both the blade mounting portion 4 and the base portion 6.

Although the beveled shoulder portion 9 of the blade 2 and the complementary delimiting edge of the second stopper 18 are of a simple linear configuration in the illustrated embodiment, other geometrical shapes may be apparently employed, provided that a firm or snug engagement can be assured.

Further, the slot 7 and the latch member 15 may be of any other shape so far as the latch 15 can pass through the slot 7 and prevent the blade 2 from slipping off at the mounted position thereof.

The knife according to the invention is particularly suited for use as the surgeon's knife.

Although the invention has been described in conjunction with the preferred embodiments, it will be appreciated that many modifications and variations will readily occur for those skilled in the art without departing from the spirit and scope of the invention.

I claim:

1. A detachable knife assembly comprising:
 a blade member including a cutting head portion integrally attached to a base portion, said base portion including an elongated aperture extending completely therethrough; and
 a profiled end portion positioned remote from said cutting head portion;
 a handle assembly formed of resiliently deformable material and including a forward end portion in contact with said blade member;
 recess means formed in said forward end portion of said handle for fixedly positioning the base portion of said blade member relative to said handle assembly;
 a stud member projecting from said recess means and including a cross-section permitting said stud member to be received within said elongated aperture;
 latch means attached to an end portion of said stud member for maintaining said base portion of said blade member within said recess means;
 stop means attached to said forward end portion and positioned on a first side of said stud member for overlapping and securing the base portion of said blade member within said recess means; and guide ridge means positioned on an opposite side of said stud from said stop means and cooperating with said stop means for permitting said resiliently deformable handle to flex a greater amount than the base portion of said blade member during attachment of said blade member to said forward end portion of said handle.

2. A knife assembly according to claim 1, wherein said elongated aperture includes a pair of opposite, substantially parallel extending side wall portions and a pair of curved, connecting wall portions extending between the side walls and positioned at either end of said aperture.

3. A knife assembly according to claim 2, wherein said latch means comprises an elongated plate having a shape similar to the shape of said elongated aperture, with said elongated plate extending substantially orthogonal to a longitudinal axis through said handle assembly, to permit insertion of said stud through said elongated aperture only when said base portion of said blade is positioned substantially orthogonal to the longitudinal axis of said handle.

4. A knife assembly according to claim 3, wherein said handle assembly further includes an elongated gripping portion integrally attached to said forward end portion.

5. A knife assembly according to claim 1, wherein said stop means comprises a support assembly including a first leg portion extending from said recess means and a second, leg portion attached to the first leg portion and extending substantially parallel to said recess means and forming a gap therebetween.

said gap having a width substantially similar to the thickness of said base portion of said blade member to allow positioning of said blade member within said gap.

6. A knife assembly according to claim 1, wherein said guide ridge means comprises an inclined ridge formed on said forward end portion and positioned adjacent to said recess means, said inclined ridge extends substantially longitudinally along said forward end portion and increases in width as the distance from said stud member increases.

7. A knife assembly according to claim 6, wherein the maximum width of said inclined ridge is less than the length of said stud member.

8. A knife assembly according to claim 6, wherein said inclined ridge is formed with a profiled edge portion confronting said recess means which is complementary in shape to the profiled end portion of said blade member.

9. A knife assembly according to claim 1, wherein an aperture is formed completely through the recess means to allow access to said blade member for cleaning and the like.

* * * * *